United States Patent [19]

Michaels et al.

[11] 4,440,853
[45] Apr. 3, 1984

[54] MICROBIOLOGICAL METHODS USING HOLLOW FIBER MEMBRANE REACTOR

[75] Inventors: Alan S. Michaels, San Francisco; Channing R. Robertson, Stanford; Stanley N. Cohen, Portola Valley, all of Calif.

[73] Assignee: Board of Trustees of the Leland Stanford Junior University, Stanford, Calif.

[21] Appl. No.: 504,599

[22] Filed: Jun. 20, 1983

Related U.S. Application Data

[63] Continuation of Ser. No. 179,591, Aug. 21, 1980, abandoned.

[51] Int. Cl.$^3$ .................. C12P 1/00; C12P 21/00; C12N 11/00
[52] U.S. Cl. .................. 435/68; 435/41; 435/174; 435/182; 435/284; 435/287; 435/813
[58] Field of Search .............. 435/287, 813, 182, 183, 435/176, 284, 68, 240, 241, 41; 210/150, 615

[56] References Cited

U.S. PATENT DOCUMENTS

| | | | |
|---|---|---|---|
| 3,821,087 | 6/1974 | Knazek et al. | 435/285 |
| 3,860,490 | 1/1975 | Guttag | 435/823 |
| 4,149,936 | 4/1979 | Messing et al. | 435/176 |
| 4,181,604 | 1/1980 | Onishi et al. | 210/615 |
| 4,184,922 | 1/1980 | Knazek et al. | 435/284 |
| 4,242,460 | 12/1980 | Chick et al. | 435/284 |
| 4,391,912 | 7/1983 | Yoshida et al. | 435/241 |

OTHER PUBLICATIONS

Kan et al., "Urocanic Acid Production Using Whole Cells Immobilized on a Hollow-Fiber Reactor", Biotechnology and Bioengineering, vol. XX, (1978), pp. 271-320.
Webster et al., Biotechnology and Bioengineering, vol. XX, (1979), pp. 1725-1748, Abstract only.
Webster et al., Biotechnology and Bioengineering, vol. XX, (1978), pp. 1273-1282, Abstract only.
Webster et al., Chemical Engineering Science, vol. 34, (1979), pp. 1273-1282.

Primary Examiner—Thomas G. Wiseman
Assistant Examiner—John Tarcza
Attorney, Agent, or Firm—Flehr, Hohbach, Test, Albritton & Herbert

[57] ABSTRACT

Methods for microbiological processing of organic materials for production of valuable products. Asymmetric hollow fibers are employed in a flow reactor, where the hollow fibers have a semipermeable membrane surrounding a lumen, where the semipermeable membrane is supported by a sponge structure. The pores of the sponge structure serve as a housing for microorganisms or cells with high density packing of the microorganisms or cells in the pores. Nutrient medium continuously flowing through the lumen provides nutrients to the microorganisms or cells as well as any substrates to be processed by the microorganisms or cells. The nutrients and substrates diffuse through the semipermeable membrane into the pores, where they are processed, and the metabolic products diffuse into the lumen. The lumen effluent is then processed for the desired products. Optionally, oxygen is provided external to the hollow fiber to enhance the amount of oxygen available to the microorganisms and cells.

8 Claims, 3 Drawing Figures

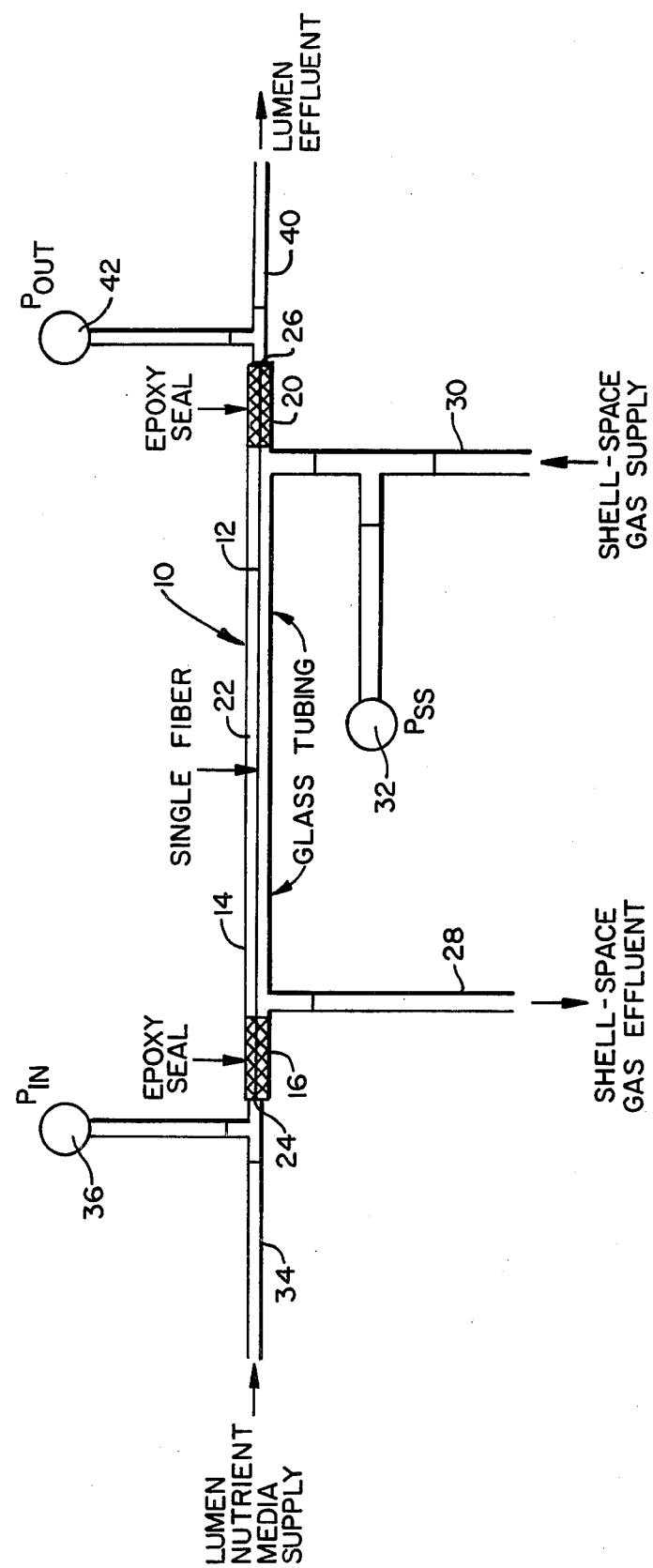
FIG._1.

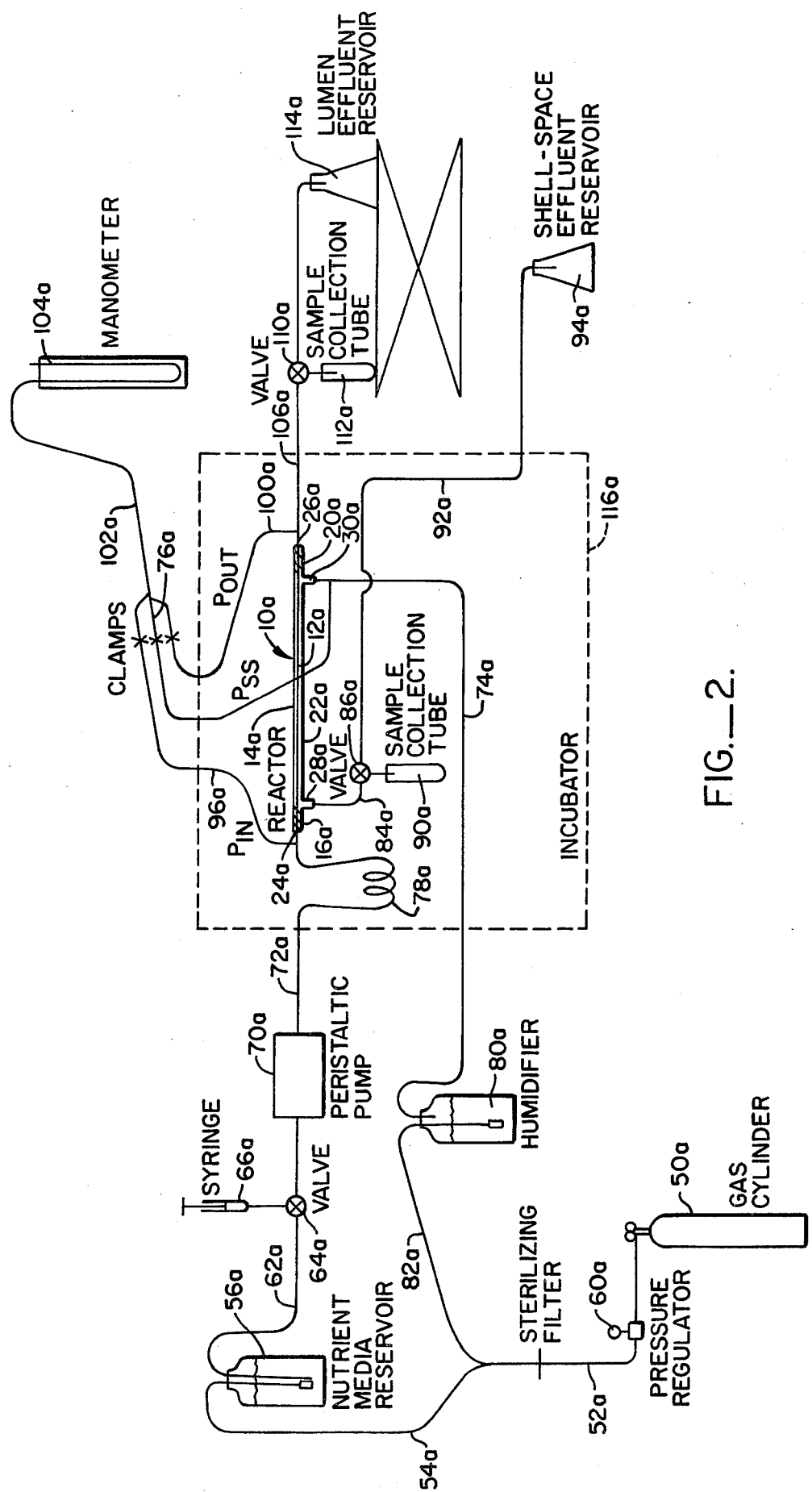
FIG._2.

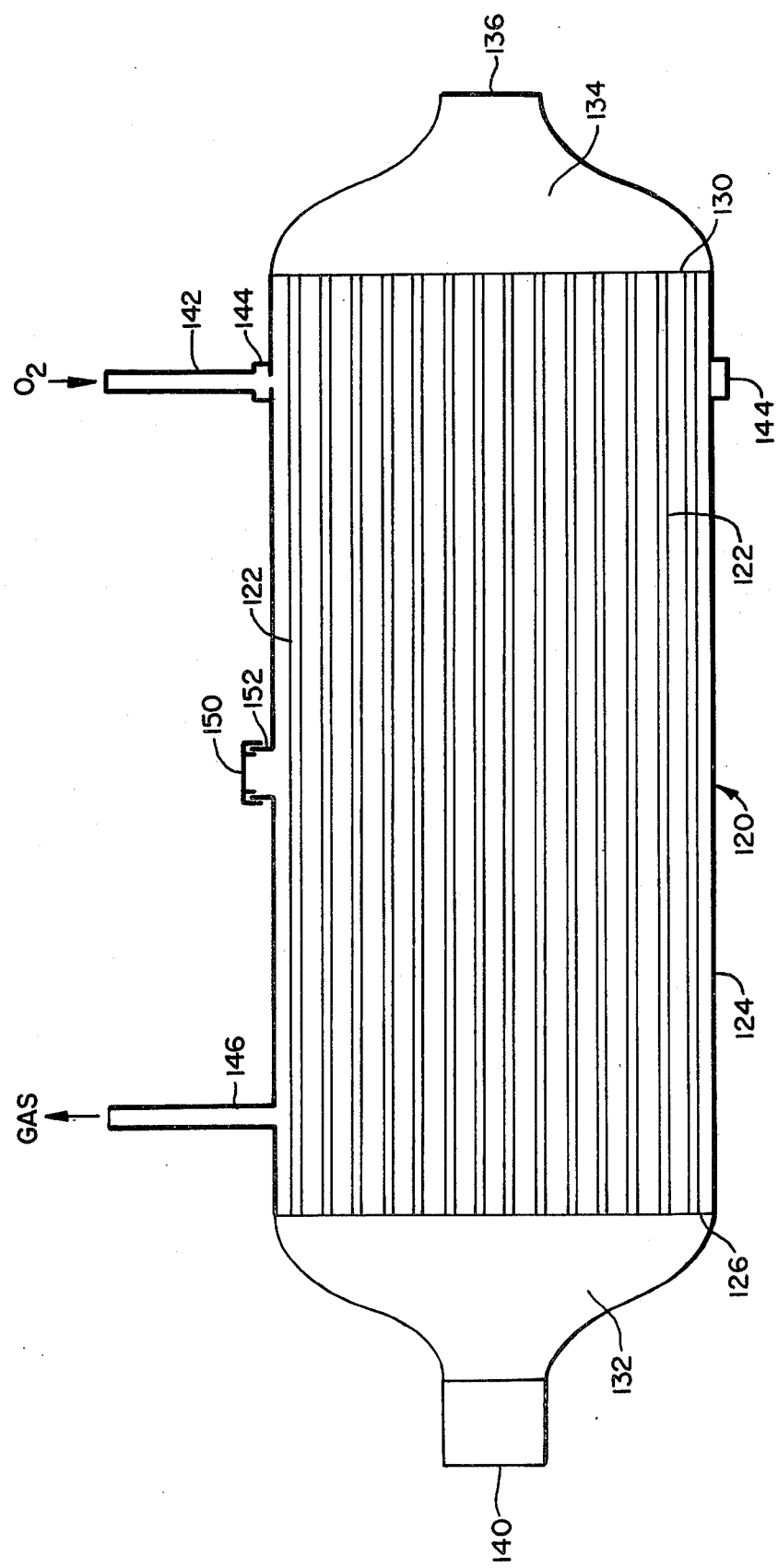

MICROBIOLOGICAL METHODS USING HOLLOW FIBER MEMBRANE REACTOR

This is a continuation of application Ser. No. 179,591, filed Aug. 21, 1980, now abandoned.

BACKGROUND OF THE INVENTION

1. Field of the Invention

Although the catalytic properties of microorganisms have been exploited in various biochemical processes for years, the techniques generally employed to carry out these transformations have their origins in traditional batchfermentation methods, and have undergone little change since their original initiation. With the relatively recent appearance of recombinant DNA techniques for genetically altering cellular function and metabolism, there is an increasing need to improve the exploitation of microorganisms to produce valuable products or process effluent streams. There is little known about the dynamics of cell growth. The ability to supply nutrients to the cell organisms, the manner in which the organisms become distributed in a reactor, the effect on such distribution of the supply of nutrients to the organisms and the removal of excretion products from the organisms remains a matter of uncertainty. In addition to the concerns about distribution of nutrients and removal of excretion products, the fragile nature of the cells limits the manner in which the cells may be handled during the processing. Techniques which have found application include fermenting involving mechanical agitation and a flowing stream through a reactor for supplying nutrient and removing product; air-lift fermentors; fluidized-bed fermentors; immobilized cells and the like.

In order to maximize the benefits of using microorganisms, substantial improvements are required in the yields of product obtained employing microorganisms where the yield is based on per unit of reactant as well as per unit volume of rector, the packing density of the microorganisms, the rate of production, the viability of the organisms, and the like.

2. Description of the Prior Art

U.S. Pat. No. 3,580,840 describes a method and apparatus using microorganisms for sewage treatment employing a porous membrane. U.S. Pat. No. 3,767,790 teaches microorganism entrapment for controlled release. See also U.S. Pat. No. 3,860,490. U.S. Pat. No. 3,875,008 teaches microorganism encapsulation in a hollow filament. U.S. Pat. No. 4,148,689 teaches entrapment of microorganisms in a gelled sol.

SUMMARY OF THE INVENTION

Method and apparatus are provided for microbiological transformation of a nutrient stream. The apparatus employs at least one asymmetric hollow fiber having an internal membrane surrounding a lumen and a porous supporting wall. A nutrient medium flows through the lumen providing nutrient for the microorganisms in the pores of the wall and removing microbiological products. Optionally, oxygen is provided external to the hollow fiber to enhance oxygen availability. The apparatus provides for high packing densities of microorganisms in the pores with good viability providing for enhanced efficiency in metabolizing substrates.

BRIEF DESCRIPTION OF THE DRAWINGS

FIG. 1 is a schematic view of a single fiber reactor;

FIG. 2 is a flowchart of a single fiber reactor providing for monitoring the streams entering and exiting from the reactor; and FIG. 3 is a cross-sectional view of a multifiber reactor.

DESCRIPTION OF THE SPECIFIC EMBODIMENTS

Novel reactors and method employing the reactor are provided for microbiological transformations. The reactors employ at least one, normally a plurality of asymmetric hollow fibers which are conveniently mounted in parallel in a closed housing. For the purposes of this invention, microorganisms will be used as illustrative of single cells which can be cultured in vitro. It should be appreciated that the subject invention is applicable to single cell lines, particularly proliferative single cell lines.

The microorganisms are inoculated into the fluid in the space surrounding the hollow fibers, while a nutrient medium is directed to the lumen of the hollow fibers. The nutrients and substrates pass, by flowing or diffusing into the pores of the hollow fiber wall containing the microorganisms, while the microbiological products flow or diffuse back into the lumen and into the interfiber spaces. In this way, nutrient continuously washes the microorganisms in the pores and products are removed from the pores to prevent inhibition of the microorganism metabolism.

The hollow fibers which are employed are asymmetric hollow fibers having a thin internal porous membrane supported by a relatively thick porous wall. The orifices of the inner membrane will generally have molecular weight cut-offs of less than about 200,000, preferably less than about 100,000, and may be 50,000 or less, usually not less than about 5,000, more usually not less than about 10,000 molecular weight. The choice of molecular weight cut-off will be determined by the degree to which microorganisms are inhibited from entering the lumen, while allowing for diffusion or flow of desired materials between the lumen and wall pores of the hollow fiber.

The purpose of the inner membrane is to inhibit cell leakage into the lumen and to provide molecular separation capability, while permitting a relatively rapid rate of diffusion and flow of solutes between the lumen and wall pores. Generally, the thickness of the inner membrane will be not less than about $0.01\mu$ and not more than about $1\mu$, more usually not more than about $0.5\mu$. The diameter of the orifices of the inner membrane will generally be from about one to two orders of magnitude smaller than the smallest dimension of the microorganism being cultivated. For bacteria, this will usually be from about $0.001\mu$ to about $0.005\mu$, while for larger cells, larger orifices will be acceptable.

The porous supporting wall surrounds the inner membrane and supports the inner membrane, with the pores or cavities of the wall communicating through the orifices of the inner membrane with the lumen. The thickness of the wall is not critical to this invention, although beyond a certain thickness, providing for nutrients throughout the pores may become difficult. The outer wall will therefore be of from about 50 to 500 microns thick, more usually from about 75 to 400 microns thick and preferably of from about 100 to 200 microns thick. Outer diameters of the fiber will generally vary from about 0.25 mm to about 2.5 mm.

The porous wall or outer region of the fiber will be mostly void space, there being at least 50% void space, more usually at least 60% void space and usually not more than about 90% void space, more usually from about 65 to 85% void space. This region is normally termed the sponge region. The pores of the wall will have relatively free access to the outside, the openings generally being at least about 5μ and may be 10μ or greater, usually being not greater than about 50μ on the average. The openings are large enough for the microorganism of interest to enter the pore. The volume of individual pores will be sufficient to house at least about $10^2$ cells, usually at least about $10^3$ cells.

The length of the fiber in the reactor can be varied widely depending upon the rate at which the fluid flows through the lumen, the potential for further transformation of the desired product, the efficiency and rate at which the desired substrate is transformed, the pressure drop across the lumen and other process considerations. Lengths will usually be at least about 1 cm, more usually at least about 5 cm, and may be 50 cm or longer.

The diameter of the lumen may vary widely depending upon the desired rate of flow, the rate of flow and diffusion of nutrients into the pores, the efficiency of utilization of the nutrients in the nutrient medium and the desired concentration of product. The ratio of the diameter of the lumen to the diameter of the fiber will vary widely, usually being at least about 20% and generally not more than about 90%, the above considerations affecting the ratio. The significant factor in the ratio is the greatest path length nutrient must flow to feed all of the cell population and the ability to provide adequate amounts of nutrients across that path length. Therefore, the wall and the cell nutrient requirements will play a role in the hollow fiber design.

A wide variety of materials are employed for the production of asymmetrical hollow fibers. The particular material is not a critical part of this invention, so long as it does not deleteriously affect the growth of the microorganisms nor react with the nutrients and products. Various inert polymeric materials can be employed, both organic and inorganic, and a numbers of hollow fibers are commercially available. Illustrative hollow fiber membranes include polysulfone membranes, terpolymers of vinyl chloride, vinylidene chloride and acrylonitrile (available as Dynel ®) polypropylene membranes and cellulosic membranes (available as Cuprophan ®). The materials may be hydrophilic or hydrophobic or combinations thereof. If desired, the various materials may be further modified to introduce functionalities onto the fiber.

While a reactor having a single hollow fiber may be employed, for the most part a plurality of fibers will be employed in a single housing or shell. The housing will enclose the hollow fibers so that the fibers are washed in the nutrient medium which flows out of the pores of the hollow fiber. One or more ports may be provided in the shell for introducing materials external to the fibers, for sampling, for removal of gases, for removal of the product containing spent nutrient stream for isolation of product and recycling of nutrients, for adding nutrients, or the like. The housing may also be used for maintaining a pressure differential between the lumen and the outside of the hollow fiber. The packing of the hollow fibers in the shell will vary depending upon the desirability of having microorganisms grown outside the pores of the shell, the ability for diffusion between the hollow fibers and the volume outside the fibers in the shell, and the ease with which oxygen can be diffused through the medium. For the most part, the packing will be determined empirically and will vary with the nature of the microorganism, as well as the purpose of the reactor.

A wide variety of microorganisms and cells may be grown in the reactor. Particularly, bacteria, yeast and fungi can be effectively grown. Not only can naturally occurring microorganisms and cells be employed, but also microorganisms and cells which have been modified by conjugation or genetic engineering techniques, such as transformation, DNA insertions, transduction, fusion and the like. Among cells which may be grown in the reactor are various mammalian cells which can be cultured in vitro, particularly tumor cells and hybridomas.

Cells can be employed in which DNA replication is substantially inhibited or terminated, but metabolism continues for relatively long periods of time. The cells continue to express genes, other than the blocked genes involved with DNA replication. Where the cells have been transformed with exogenous genes, these genes will be expressed to provide the desired product.

By preventing DNA replication, the nutrients are used more efficiently for the functioning of the microbiological reactor. The inhibition of DNA replication can be achieved in a variety of ways, such as chemical inhibitors, temperature sensitive mutants, mutants lacking an intermediate in the biosynthetic pathway to DNA replication, or the like.

The nutrient medium employed will be dependent upon the microorganism or cell involved, and the product desired or purpose for the reactor. For example, the nutrient medium will be adapted to the particular microorganism or cell. Besides nutrients, other substances may be included to support growth and/or cell differentiation. By contrast, the product may be a natural product such as an excreted protein e.g. enzymes, hormones, lymphokines, toxins, immunoglobulins, or the like or a non-proteinaceous organic compound resulting from transformation of a substrate, such as by epoxidation, hydroxylation, esterification e.g. acetate, phosphate, uronate or sulfate, reduction, methylation, etherification with sugars, or the like. Thus, the reactor can act as a source of a wide variety of compounds, either as the natural product, such as a polypeptide or protein, or for transforming a synthetic substrate. Alternatively, the reactor may be used with a wide variety of effluents from various commercial processing sources, such as chemical processing plants, sewage plants, water treatment plants, or the like.

Besides nutrients provided in the lumen, additional nutrients may be provided in the shell space. Particularly, because of the low solubility of oxygen in water, additional oxygen may be provided into the fluid surrounding the hollow fibers. To further enhance oxygen content, the fluid and shell space may be pressurized so that the concentration of oxygen in the nutrient solution is increased.

During operation, the cells substantially fill the wall pores to greater than 50% of the available volume, usually greater than 60% and cell densities filling greater than 80% of the void volume are achievable. The high cell packing density is realized because of the efficiency of introduction of nutrients and oxygen into the wall pores as well as the efficient removal of product from the wall pores.

For further understanding of the invention, the drawings will now be considered. The reactor 10 is comprised of a single hollow fiber 12 which is centrally extended in a glass tube 14 and sealed at its ends in the tube 14 by seals 16 and 20. Seals 16 and 20 enclose the space 22 in tube 14. The fiber extends to the ends of seals 16 and 20 so as to provide inlet port 24 and exit port 26 for introduction and removal respectively of the nutrient medium. To provide for the opportunity for additional oxygen supply to the shell space 22, as well as for monitoring gas production in the shell space 22, conduits 28 and 30 are connected to the tube 14 in fluid transfer relationship internal to the seals 16 and 20. A manometer 32 is attached to conduit 30 for monitoring the pressure of the gas supply or if desired, the pressure in space 22. Connected to the inlet port 24 is inlet conduit 34 equipped with pressure gauge 36 for monitoring the pressure of the inlet nutrient stream. Outlet conduit 40 is connected to outlet port 26 in fluid receiving relationship and a pressure gauge 42 is mounted on the outlet conduit 40 to provide for monitoring the pressure of the lumen effluent. In addition to providing for the introduction of gas or other materials into the shell space 22, conduits 28 and 30 also provide the opportunity to innoculate the reactor with microorganisms or cells.

FIG. 2 is a diagram of the equipment used in a number of tests. The reactor 10a has a single fiber 12a which is sealed in the tube 14a by seals 16a and 20a. Pressurized oxygen is provided by gas cylinder 50a, which is connected by lines 52a and 54a to nutrient media reservoir 56a. Pressure regulator 60a mounted in line 52a controls the oxygen pressure in line 52a. The oxygen pressure forces the nutrient media in reservoir 56a into line 62a in which is mounted three-way valve 64a, the remaining arm being fitted with syringe 66a. Line 62a connects with peristaltic pump 70a which controls the flow of the nutrient medium through line 72a to inlet port 24a of hollow fiber 12a. Line 72a has a series of coils 78a to allow for temperature control of the nutrient medium fed to hollow fiber 12a. Side arm 30a of tube 14a is connected by a conduit 74a to shell space sampling conduit 76a and humidifier 80a. The humidifier 80a is connected by means of conduit 82a to line 52a to permit humidified oxygen to be introduced into the reactor shell space 22a. Side arm 28a is connected by means of line 84a to three-way valve 86a which serves to pass the effluent from the shell space 22a into sample collection tube 90a or by means of line 92a to shell-space effluent reservoir 94a.

The nutrient media fed into inlet port 24a by means of line 72a are monitored through line 96a, while the lumen effluent exiting exit port 26a is monitored through line 100a. Lines 76a, 96a, and 100a are all connected to line 102a which is connected to a manometer 104a for monitoring the pressure in the reactor. The nutrient medium of the lumen exiting through exit 26a is connected by line 106a to three-way valve 110a which serves to connect the effluent to sample collection tube 112a or lumen effluent reservoir 114a. For temperature control, the reactor and portions of the components connected to the reactor may be maintained in an incubator 116a indicated by the broken lines.

FIG. 3 depicts a multihollow fiber reactor 120 having a plurality of hollow fibers 122 in a housing or shell 124. The hollow fibers 122 are mounted on manifold discs 126 and 130 which serve to hold the hollow fibers in position while allowing access between the hollow fibers 122 and chambers 132 and 134. Chamber 134 has inlet port 136 while chamber 132 has outlet port 140. Gas inlet conduit 142 connects to gas manifold 144 which distributes the gas evenly about the periphery of the housing 124. Gas outlet 146 is provided to control the pressure in the reactor 120. The reactor is provided with a septum 150 mounted on side arm 152. The septum permits the innoculation of the reactor with cells and removal of samples without disturbing the reactor.

In studying the subject reactor, reactors having from 20 to 40 fibers were studied. The asymmetric hollow fibers employed were obtained from Amicon Corporation. The fibers are resistant to acids, alkalines and water-organic solvent mixtures with organic solvent concentrations of up to 50%. The fibers have a relatively dense inner wall which serves as a semipermeable membrane, being approximately $0.1–1.0\mu$ thick. The hollow fibers employed have molecular weight cut-offs for the membranes between 10,000 daltons and 60,000 daltons. The maximum pore diameter for the upper range of molecular weight cut-off is about $0.01\mu$, which is about 1-2 orders of magnitude less than the minimum dimension of most microbial cells. The remainder of the wall-thickness provides support for the inner membrane and is approximately $100–200\mu$ thick, with 70-80% of the volume in the outer region void space. The fiber wall has pore sizes of the order of $10\mu$. The fiber studied had outer diameters ranging from about 0.5 mm to 1.2 mm and fiber lengths were about 25 cm.

The organism studied was the bacterial strain E. coli C600 transformed with pBR322. For the purpose of the subject study, the production of $\beta$-lactamase was studied.

The E. coli strain propagates at extremely high rates, undergoing cell division about every 20-30 mins. The transformed bacteria produce $\beta$-lactamase at a rate approximately 50 times greater than the wild type strain.

The reactor employed is depicted in FIG. 2. The cultures were maintained at a temperature of 37° C. and a pressure of approximately 1 atm. The fiber employed was Amicon PW-60, 25 cm long, mounted in a 5 mm O.D. glass tube. The culture growth medium was a rich medium containing 10 g tryptone, 10 g NaCl, and 5 g yeast extract per liter of water, pH 6.5-7.5. In addition, $20\mu$ g/ml of thymine was added. The nutrient medium was saturated with pure oxygen at 1 atm before perfusion through the reactor and humidified oxygen gas at 1 atm was continuously passed through the reactor shell space following the inoculation procedure. Besides following the production of $\beta$-lactamase, the cell density in the reactor was also monitored. For the E. coli cultures, cell densities of $2 \times 10^{12}$ cells/ml of void space in the sponge region were observed. This density corresponds to the situation in which the volume of the cells accounts for 60-70% of the available space within the fiber wall. In conventional fermentation processes where significant attempts have been made to attain high cell densities, the highest densities reported are between $1 \times 10^{10}$ and $1 \times 10^{11}$ cells/ml of suspending medium. If the productivity of the reactor system is the same per cell, the subject reactor provides a significant reduction in the reactor volume for a given reactor production rate. In a few instances, cell packing densities were observed which were nearly 100% of the available space, with the hollowfiber culture appearing as a tissue cell mass analogous to the situation seen in the body where blood capillaries supply the body's tissue cells.

β-Lactamase production by *E. coli* cultures was obtained from dead cells, rather than by excretion, and continued at significant levels for at least three weeks and no fall off in enzyme productivity was observed at the time of termination. The β-lactamase production rate, expressed in terms of units enzyme activity/cell-hr was only 1% of that measured in a comparable batch shaker-flask culture conducted for comparison. However, if the β-lactamase productivity is expressed in terms of units enzyme activity/volume of reactor-hr., the hollow fiber reactor is producing at a rate of 100 times higher than the productivity measured in the shaker-flask culture. Therefore, while the reactor under relatively non-optimum conditions was not performing as well as a shaker-flask culture on a cell basis, on a reactor volume basis, the culture was approximately two orders of magnitude more productive than the comparable shaker-flask culture. Enzyme concentrations of 0.2–0.4 units/ml were achieved.

It is evident from the above results, that the subject invention provides a highly efficient compact reactor, where extremely high cell densities can be achieved. By providing optimum conditions for diffusing the nutrients into the pores of the hollow fibers, substantially all of the void space of the hollow fiber walls can be filled with cells and rapid and efficient metabolism of substrates in the nutrient medium and the lumen achieved. By virtue of the effective nutrient distribution good viability of the cells is maintained for long periods of time, so that the reactor maintains a high efficiency. By recycling, enhanced conversion of substrates can be achieved. Furthermore, relatively few cells pass into the lumen, so that the removal of the cells from the nutrient medium stream can be effectively achieved. By employing the subject reactors with microorganisms or other cells, high yields may be obtained of a wide variety of naturally occurring compounds or of enzymatically transformed products.

Although the foregoing invention has been described in some detail by way of illustration and example for purposes of clarity of understanding, it will be obvious that certain changes and modifications may be practiced within the scope of the appended claims.

What is claimed is:

1. A method for continuously transforming a substrate to a product by microbiological means employing microorganisms in a flow reactor, said flow reactor comprising:

a housing;

at least one hollow fiber in said housing, said hollow fiber having an inlet port and an outlet port and characterized by having a lumen, a porous membrane surrounding said lumen and having orifices smaller than said microorganisms, said orifices having a maximum diameter of about 0.01 micron, and a spongy supporting wall having asymmetric pores internally communicating through said orifices with said lumen and externally communicating with the volume enclosed by said housing through openings of a size greater than said microorganisms, said openings having a diameter of at least 5 microns; and a nutrient medium pervading said housing;

said method comprising:

growing microorganisms in said housing under conditions and for a period of time whereby at least 60% of the available volume of said pores in said supporting wall is occupied by said microorganisms at a cell density greater than $10^{12}$ viable cells/ml., while continually passing substrate containing nutrient medium into said lumen through said inlet port, whereby nutrients and substrate flow into said pores and said substrate is transformed to product by said microorganisms, said product diffusing back through said orifices into said lumen; and continuously removing nutrient medium containing product from said lumen through said outlet port.

2. A method according to claim 1, wherein oxygen is introduced into said housing in the volume surrounding said hollow fiber.

3. A method according to claims 1 or 2, wherein said microorganisms are prokaryotic.

4. A method according to claim 3, wherein said product is a polypeptide.

5. A method according to claims 1 or 2, wherein said microorganisms are eukaryotic single cells.

6. A method according to claim 5, wherein said cells are yeast microorganisms.

7. A method according to claim 5, wherein said microorganisms are fungi.

8. A method according to claim 1, wherein said microorganisms are bacteria and said orifices in the porous membrane have a diameter in the range from about 0.001 to 0.005 micron.

* * * * *